United States Patent [19]

Stein

[11] 4,391,279

[45] Jul. 5, 1983

[54] ELECTRODE BELT

[75] Inventor: Israel M. Stein, Brookline, Mass.

[73] Assignee: Clinical Data, Inc., Brookline, Mass.

[21] Appl. No.: 329,646

[22] Filed: Dec. 11, 1981

[51] Int. Cl.³ .............................................. A61B 5/04
[52] U.S. Cl. .................................... 128/643; 128/644
[58] Field of Search ................................ 128/639–641, 128/643–644, 783, 798, 802, 803

[56] References Cited

U.S. PATENT DOCUMENTS

| | | | |
|---|---|---|---|
| 3,888,240 | 6/1975 | Reinhold, Jr. et al. | 128/644 |
| 4,088,133 | 5/1978 | Twentier | 128/644 X |
| 4,122,843 | 10/1978 | Zdrojkowski | 128/644 |
| 4,237,886 | 12/1980 | Sakurada et al. | 128/303.13 |

Primary Examiner—Lee S. Cohen
Assistant Examiner—Christine A. Fukushima
Attorney, Agent, or Firm—Martin Lukacher

[57] ABSTRACT

An electrode belt made up of a strip of pile-backed foam on which a sheet of conductive silicone rubber is mounted by a snapped together fastener which clamps the sheet to the belt and compresses the sheet to form a suction cup when the belt is applied against the skin of the patient, especially when coated with conductive gel or water. The snap fastener provides means for convenient connection to the electrode leads for an apnea detector, an electro-cardiograph or a recorder for pneumogram or cardiogram signals which are transmitted through the conductive sheet and the fastener to the leads.

8 Claims, 5 Drawing Figures

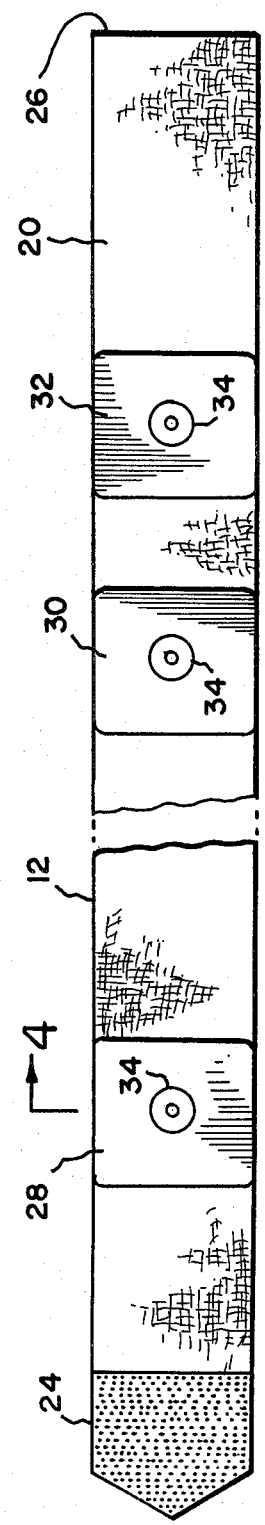
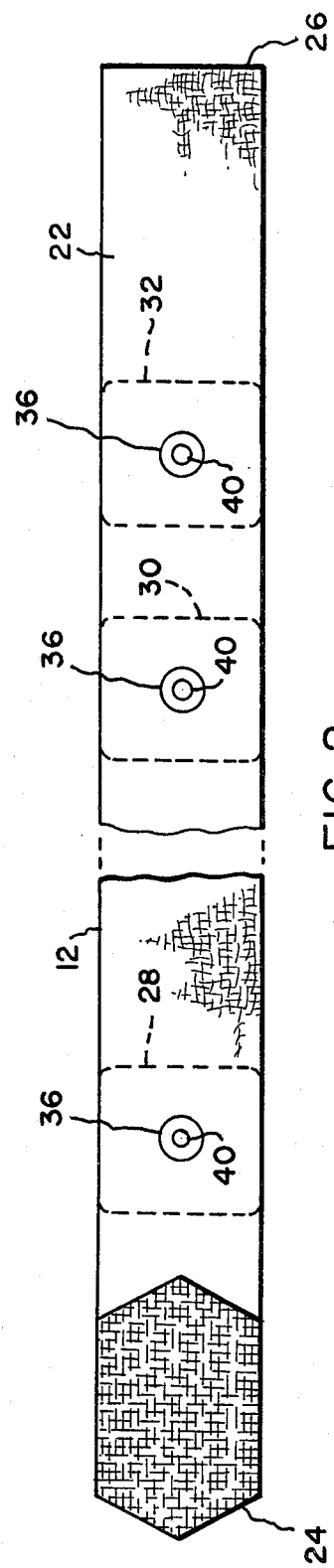
FIG. 3
FIG. 2

ELECTRODE BELT

DESCRIPTION

The present invention relates to an electrode belt which can be used for the monitoring of signals representing pulmonary or cardiac events.

The invention is especially suitable for use with infants with an apnea detector and/or with devices for recording electro-cardiographic signals. The invention is also generally useful with patients of all ages.

Making connections to the skin of an infant for prolonged periods of monitoring for apnea or heart rhythm disturbances is difficult. Skin irritation must be avoided and good contact must be maintained in spite of movement and agitation of the infant. Attachment with adhesives oftentimes leads to skin irritation. Severe constraints are unacceptable, since they can interfere with infant breathing.

It is a feature of this invention to provide an infant electrode belt which can be comfortably worn, as by an infant around its chest, and which has electrodes of such design as to maintain comfort while making good conductive contact to the skin.

It is a further feature of the invention to provide an electrode belt which is washable and may be reused.

Briefly described, an electrode belt in accordance with the invention includes a strip of soft pliable material with a sheet of conductive, flexible and compliant material, such as conductive silicone rubber to provide an electrode pad. The pad is attached to the belt with a fastener having opposed plates. Preferably, a snap fastener is used. The plates clamp the pad to the strip. The pad and strip have adjacent sides in contact. The sides opposite to these adjacent sides are clamped together to form a cup shape depression which provides a suction cup area. When the pad is placed on the skin, preferably after having water or conductive gel applied thereto, a good contact, which is maintained without skin irritation, is made. The belt may be held around the chest with one or more pad and fastener assemblies through the use of a buckle. The buckle may be a strip of hook type closure material (e.g., Velcro material) which attaches to the backing of the belt. The belt is preferably foam material having a pile backing to which the strip of hook type closure material readily attaches itself.

The foregoing and other objects, features and advantages of the invention will become more apparent from a reading of the following description in connection with accompanying drawing in which:

FIG. 2 is a plan view of the outside of the belt.

FIG. 3 is a plan view of the inside of the belt;

Figure 1:
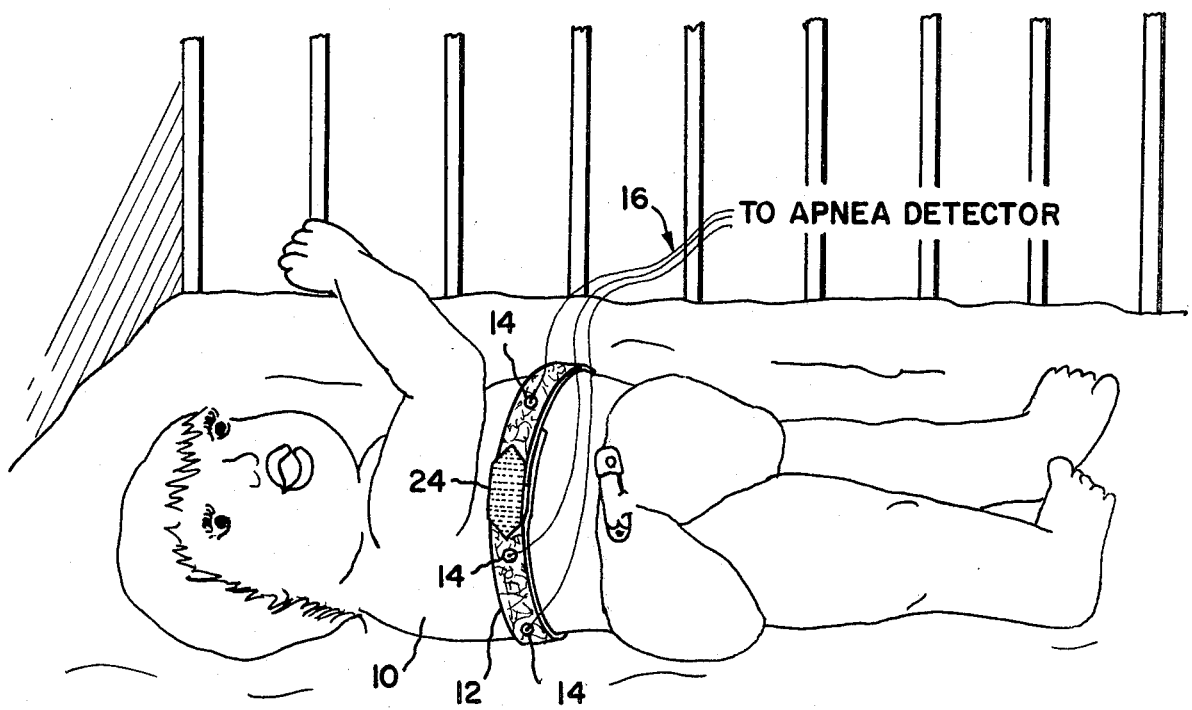
FIG. 1 is a perspective view of an infant wearing a belt provided by the invention.
Figure 4:
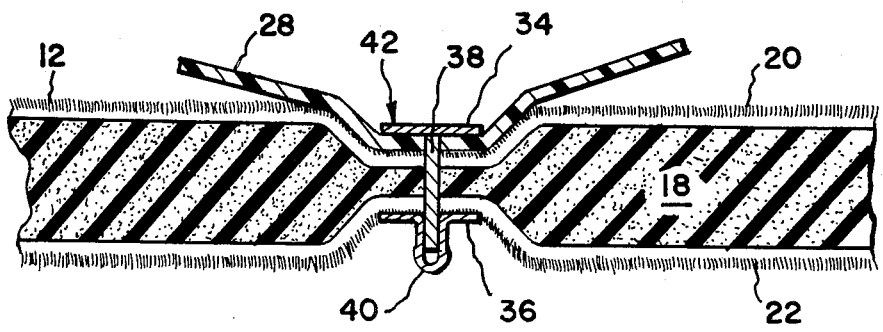
FIG. 4 is a sectional view along line 4—4 of FIG. 3.
Figure 5:
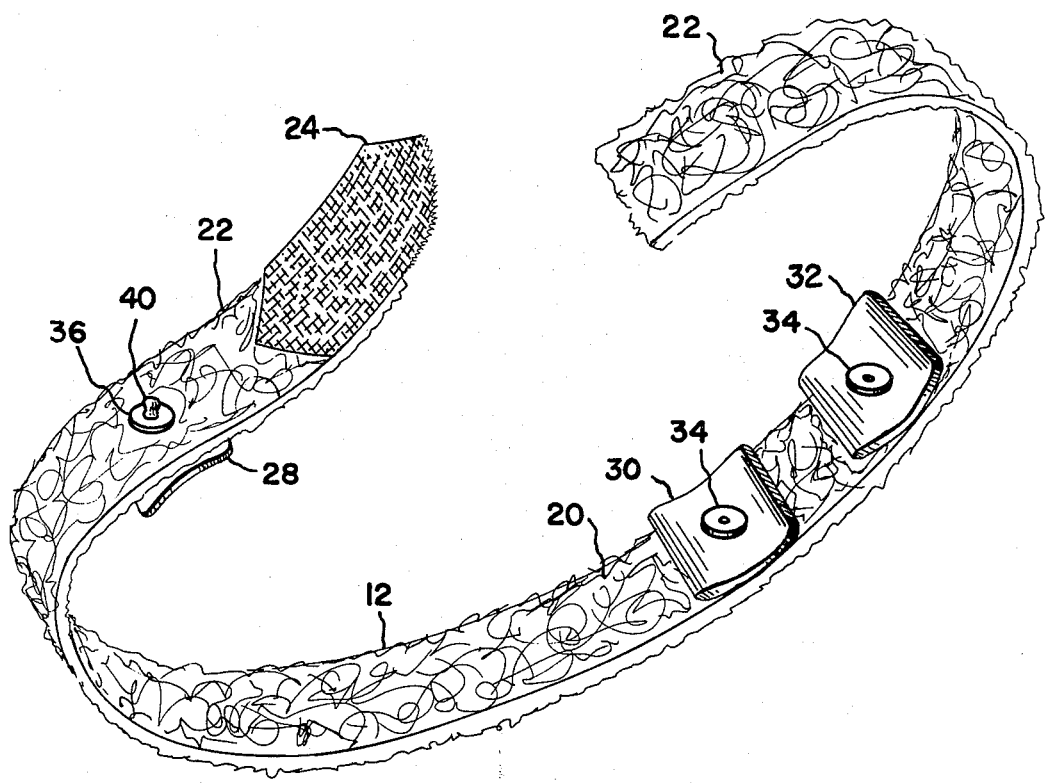
FIG. 5 is a perspective view of the belt.

Referring to FIG. 1, an infant 10 being monitored has a belt 12 provided with the invention around its chest. Leads 16 are attached to connectors 14 on the outside of the belt 12. These connectors attach electrode pads to the inside of the belt. The leads 16 go to an apnea detector and may also go to an electrocardiograph or a recorder for pneumogram and/or electrocardiogram signals.

Referring to FIGS. 2, 3, 4 and 5, the belt 12 is a strip of soft pliable material, suitably two inches wide and eighteen inches long, so as to fit around the chest of infants of different sizes. The belt is composed of a core 18 of plastic foam. The belt has backings 20 and 22 of pile material, for example of nylon or non-woven material, which is attached to the foam by laminating. The belt is compressible because of the material thereof. A buckle 24 of hook type closure material (e.g., Velcro material) is attached to the pile backing on the outside of the belt at one end thereof. When the belt is brought around the infant'chest the free end of the buckle 24 may be attached to the backing in an area thereof on the opposite end 26 of the belt, spaced a sufficient distance to comfortably fit the belt around the infant's chest.

A plurality of electrode pads 28, 30 and 32 are attached to the belt, spaced from each other to be in proximity to the areas on the chest from which electrocardiogram (cardiac) or pneumogram (pulmonary) signals are to be derived. These pads 28, 30 and 32 are similar. The pad 28, for example, is a sheet of conductive and flexible and impervious material, preferably silicone rubber. The sheet providing the pad 28 is attached to the belt strip 12 by a conductive snap having opposed plates 34 and 36. The plate 34 is an eyelet plate having a prong 38 extending therefrom. The plate 36 is a flange of a snap 40. The prong 38 is press fit into the snap 40 so that the plates 34 and 36 compress the flexible material of the belt core 18. A depression 42 provides a suction cup area. This area is desirably moistened with water from a saline solution, which is conductive or, more preferably, with conductive gel. Accordingly, when the pad 28 is in place against the skin of the infant, suction assists in making good conductive contact between the electrode, the inside plate 34 and the skin of the infant.

The leads 16 may have female snaps on fasteners (not shown) at the end thereof. The snap 40 provides means for attachment of the leads which may be snapped on to the snaps 40, preferably before attaching the belt around the chest of the infant.

The film adherence of the electrode to the position at which it is placed on the infant's chest by suction provides for good contact which reduces artifacts in the signals derived by the electrodes. The need for adhesives which may cause skin irritation is avoided. Accordingly, the belt may be used for prolonged periods of monitoring. The belt is also washable and reusable.

From the foregoing description it will be apparent that there has been provided an improved electrode belt. Variations and modifications in the belt illustrated herein, within the scope of the invention, will undoubtly suggest themselves to those skilled in the art. Accordingly, the foregoing description should be taken as illustrative and not in a limiting sense.

I claim:

1. An electrode belt which comprises a belt of soft pliable material, a sheet of conductive, flexible, compliant, impervious material providing an electrode pad having opposite surfaces, one of which is disposed upon said belt and the other against the wearer when the belt is on the wearer, a fastener of conductive material having opposed plates disposed in clamping relationship with said pad and belt therebetween to form a depression in said pad of cup shape to provide a suction area between the skin of the wearer, the pad and one of said plates, said fastener having means providing an attachment for an electrode lead.

2. The electrode belt according to claim 1 wherein said fastener is a snap together fastener which includes said plates, a prong extending from one of said plates through said pad and said belt, a snap having a flange forming the other of said plates, said snap having an opening therein which receives said prong in press fit relationship, said snap providing said electrode lead attachment means.

3. The electrode belt according to claim 2 wherein a plurality of assemblies of said pads and snap together fasteners is disposed along said belt in spaced relationship with each other.

4. The electrode belt according to claim 1 wherein said sheet consists essentially of conductive silicone rubber.

5. The electrode belt according to claim 4 wherein said pad is of rectilinear shape about equal in width to the width of said belt.

6. The electrode belt according to claim 4 wherein said belt is a strip of pile backed foam material.

7. The electrode belt according to claim 6 further comprising a strip of hook type closure material attached to the pile backing on the outside of said belt to provide a buckle.

8. The electrode belt according to claim 1 wherein said fastener provides the exclusive connection between said pad and said belt.

* * * * *